United States Patent
Metzner et al.

(10) Patent No.: US 7,276,235 B2
(45) Date of Patent: Oct. 2, 2007

(54) TISSUE GLUE WITH IMPROVED ANTIADHESIVE PROPERTIES

(75) Inventors: Hubert Metzner, Marburg (DE); Peter Gronski, Marburg (DE); Gerhard Dickneite, Marburg (DE); Monika Kroez, Lahntal (DE)

(73) Assignee: ZLB Behring GmbH, Marburg (DE)

( * ) Notice: Subject to any disclaimer, the term of this patent is extended or adjusted under 35 U.S.C. 154(b) by 701 days.

(21) Appl. No.: 10/199,018

(22) Filed: Jul. 22, 2002

(65) Prior Publication Data

US 2003/0133928 A1 Jul. 17, 2003

Related U.S. Application Data

(63) Continuation-in-part of application No. 09/856,195, filed as application No. PCT/EP99/08812 on Nov. 16, 1999, now Pat. No. 6,447,774, and a continuation-in-part of application No. 09/861,657, filed on May 22, 2001, now abandoned.

(30) Foreign Application Priority Data

Nov. 18, 1998 (DE) ................................ 198 53 033
May 22, 2000 (DE) ................................ 100 25 001

(51) Int. Cl.
*A61K 38/48* (2006.01)
*A01N 37/18* (2006.01)
(52) U.S. Cl. ........................................ 424/94.64; 514/2
(58) Field of Classification Search ............. 424/94.64; 514/2
See application file for complete search history.

(56) References Cited

U.S. PATENT DOCUMENTS

| | | | |
|---|---|---|---|
| 4,427,651 A | 1/1984 | Stroetmann | |
| 4,453,939 A | 6/1984 | Zimmerman et al. | |
| 5,290,918 A | 3/1994 | Bui-Khac | |
| 5,330,974 A | 7/1994 | Pines et al. | |
| 5,525,648 A | 6/1996 | Ansen et al. | |
| 5,605,887 A * | 2/1997 | Pines et al. | 514/21 |
| 5,795,571 A | 8/1998 | Cederholm-Williams et al. | |
| 5,804,428 A * | 9/1998 | Edwardson et al. | 435/212 |
| 5,962,405 A | 10/1999 | Seelich | |
| 6,084,074 A * | 7/2000 | Kato et al. | 530/381 |
| 6,096,309 A * | 8/2000 | Prior et al. | 424/94.63 |
| 6,121,232 A * | 9/2000 | Nur et al. | 514/2 |

FOREIGN PATENT DOCUMENTS

| | | |
|---|---|---|
| DE | 1966-22256 F * | 6/1965 |
| DE | 198 53 033 A1 | 5/2000 |
| DE | A-10012732 | 9/2001 |
| EP | 0 554 570 A2 | 8/1993 |
| EP | 0 804 933 A2 | 11/1997 |
| WO | WO 92/22312 | 12/1992 |
| WO | WO 93/05067 | 3/1993 |
| WO | WO 99/11301 | 3/1993 |
| WO | WO 94/00566 | 1/1994 |
| WO | WO 96/22115 | 7/1996 |
| WO | WO 97/28832 | 8/1997 |
| WO | WO 99/29338 | 6/1999 |
| WO | WO 00/29041 | 5/2000 |

OTHER PUBLICATIONS

Abstract for DE 1,493,614, Neuland et al., "Antifibrinolytic c-aminomethylbenzoic acid esters," Jun. 5, 1965, Derwent database.
Abstract for EP 0 554 570 A2, Hock et al., "Stable fibrinogen solution", esp@net database.
Chabbat, J., et al., "Properties of a New Fibrin Glue Stable in Liquid State," *Thrombosis Research*, 76(6):525-533 (1994).
De Iaco, PierAndrea, et al., "Fibrin Sealant in Laparoscopic Adhesion Prevention in the Rabbit Uterine Horn Model," *Fertility and Sterility* 62(2):400-404 (1994).
Evrard, V.A.C., et al., "Peritoneal Healing After Fibrin Glue Application: A Comparative Study in a Rat Model," *Human Reproduction* 11(9):1877-1880 (1996).
Gauwerky, J.F.H., et al., "The Effect of Fibrin Glue and Peritoneal Grafts in the Prevention of Intraperitoneal Adhesions," *Arch. Gynecol. Obstet.* 247:161-166 (1990).
Lindenberg, S., et al., "Prevention of Peritoneal Adhesion Formation by Fibrin Sealant," *Annales Chirurgiae et Gynaecologiae* 73:11-13 (1984).
Moro, Hisanaga, et al., "The Effect of Fibrin Glue on Inhibition of Pericardial Adhesions," *The Japanese Journal of Thoracic and Cardiovascular Surgery* 47(2):79-84 (1999).
Takeuchi, Hiroyuki et al., "Effects of Fibrin Glue on Postsurgical Adhesions After Uterine or Ovarian Surgery in Rabbits," *J. Obstet. Gynaecol. Res.* 23(5):479-484 (1997).
English Translation of German Patent Application No. DE-A-10012732.
English translation of PCT/EP99/08812, which claims priority of DE 198 53 033 A1.
Cover Sheet of PCT/EP99/08812, published May 25, 2000.

* cited by examiner

*Primary Examiner*—Christopher R. Tate
*Assistant Examiner*—Randall Winston
(74) *Attorney, Agent, or Firm*—Finnegan, Henderson, Farabow, Garrett & Dunner, LLP

(57) ABSTRACT

The use of a tissue glue comprising a stabilized fibrinogen preparation, which can be stored in the liquid or frozen state and comprises a chaotropic substance, and a thrombin preparation, for reducing or preventing tissue adhesions, is described.

30 Claims, No Drawings

TISSUE GLUE WITH IMPROVED ANTIADHESIVE PROPERTIES

This application is a continuation-in-part of U.S. patent application Ser. No. 09/856,195, filed on Jul. 13, 2001, which is the U.S. national stage filing under 35 U.S.C. § 371 of International Application No. PCT/EP99/08812, filed Nov. 16, 1999, and U.S. patent application Ser. No. 09/861,657, filed on May 22, 2001, and claims priority to both applications. This application also claims priority under 35 U.S.C. § 119 of German Patent Application No. 100 25 001.7, filed on May 22, 2000, and of German Patent Application No. 198 53 033.1, filed Nov. 18, 1998, both of which are hereby incorporated by reference.

One embodiment of the invention relates to the use of a tissue glue for reducing or preventing postoperative tissue adhesions, which is distinguished from known tissue glues for its improved antiadhesive properties.

It is known that in the development of tissue glues to date, priority has been given to the hemostatic or sealing activity (e.g., against loss of CSF) of the glue. These indications still account for a very considerable number of the uses of tissue glues nowadays.

Tissue glues are commercially available either as lyophilizates or as frozen preparations. However, after reconstitution or after defrosting, the products are stable in solution for only a few days, because with the highly concentrated fibrinogen-/Factor XIII-solutions, an aggregation and therefore an (for example, proteolytic) inactivation occurs, which makes any further use impossible.

Other tissue glues that have been described in the literature until now are not yet commercially available and are generally comprised of frozen or freeze-dried components that must be defrosted or dissolved prior to use. European patent 0,085,923, German patent application 196 17 369 and European patent application 0,856,317 describe the use of chaotropic agents or additives such as arginine or urea or their derivatives or derivatives of benzene, imidazole, pyrozol, furan, thiazole and purine, which generally improve the solubility of proteins. Chaotropic agents in this context are agents that reduce or destabilize the reciprocal effect between proteins or parts thereof and therefore reduce their tendency towards aggregation. However, with liquid storage, but especially also with storage in frozen state, the loss of Factor XIII-activity in the formulations described thus far was so high that in the presence of effective quantities of chaotropic agents, the Factor XIII-content often clearly drops after only a few weeks or months, often even below the detection limit.

For example, we have shown that in the formulations in accordance with European patent application 0,856,317, tranexaminic acid (AMCA), especially in the presence of chaotropic agents such as arginine and inorganic salts, clearly reduced the Factor XIII content in the course of storage at −20° (see instant Table 1b, Batch 1). Storage at 4° Celsius leads to an increase in viscosity in this formulation (Table 1 a, Batch 1), which also rules out a long-term storage. Thus, these formulations must be considered non-stable when considering the simultaneous stability of fibrinogen and Factor XIII. Formulations in accordance with DE 196 17 369 also indicate problems in maintaining Factor XIII-activity (see instant Table 1, Batch 2 and 2).

Another biological adhesive for human or animal tissue is known from the European patent specification 0,487,713. Said adhesive is stabilized in liquid form at low temperatures. This is supposed to be achieved because the preparation containing fibrinogen comprises at least one chaotropic agent in a concentration between approximately 0.3 M and 1 M and because the adhesive is liquid at the storage temperature.

Such fibrinogen concentrate typically comprises about 4 mmol tri-sodium citrate, 240 mmol NaCl, 80 mmol-amino caproic acid (EACA), 240 mmol glycine, 1% polysorbate, 0.6 grams/liter sodium caprolate, 0.5 mol urea, 2,000 KIE/ml aprotinin, if necessary, and a pH of 7.5. The stability was evaluated after only one month, which is very short for a therapeutic preparation. The Factor XIII-activity was not analyzed. J. Chabbat et al. reported about a fibrinogen concentrate that remains stable in liquid state at 4° Celsius over a period of six months (J. Chabbat, M. Tellier, P. Porte and M. Steinbuch: Properties of a new fibrin glue stable in liquid state. Thromb. Res. 76: 525-533 (1994)). In addition to other formulation components, typically 60 mmol/liter NaCl, 20 mmol/liter EACA and 60 mmol/liter glycine, this concentration comprised 0.5 mol urea or 5% arginine (=0.29 mol). However, the Factor XIII-strength of this concentration was also not tested.

These liquid formulations, which were described in the European patent specification 0,487,713 and in the literature, are characterized in that the aggregation (polymerization) and thus the increase in viscosity of the concentrated fibrinogen component, is prevented or reduced at refrigeration temperatures. However, Factor XIII, an essential component of fibrinogen concentrates for fibrin glues, is inactivated to a greater or lesser degree under these conditions. In the formulations provided for storage in cooled state in accordance with European patent specification 0,487,713 or the related publication by Chabbat et al. (J. Chabbat, M. Tellier, P. Porte and M. Steinbuch: Properties of a new fibrin glue stable in liquid state. Thromb. Res. 76:525-533 (1994)), the instability of Factor XIII is therefore a significant problem that is not solved by the proposed formulations (see instant Table 1, Batches 4-5). Furthermore, the strength of chaotropic agents is relatively high at 0.3 to 1.0 mol/liter.

Thus, it can be noted that it was found in the analysis of the stability of fibrinogen/Factor XIII preparations as well as the viscosity of various known fibrinogen/Factor XIII-preparations in refrigerated state (0 to 10° Celsius) or frozen state with subsequent storage in refrigerated state (0 to 10° Celsius) that the previously described formulations do not lead to stable protein preparations. Either the fibrinogen or Factor XIII show a significant reduction in activity during the storage time, or the aggregation of fibrinogen leads to a viscous material that can no longer be applied (see instant Table 1, Batches 1 to 5).

Thus, one objective of the invention was to develop protein preparations that are liquid and stable over several months, or frozen and stable over several months following defrosting, in which the fibrinogen and/or Factor XIII are stabilized over months or years without any significant loss of effect.

The problem is solved with stabilized protein preparations that in comparison to the state of the art have the advantage that, in a first embodiment, not only fibrinogen but also Factor XIII are stabilized by the additives and that the content of chaotropic reactants can be reduced, or that, in a second embodiment, fibrinogen and Factor XIII are formulated separately and thus remain stable.

In one embodiment of the invention, this is achieved in that for frozen preparations and preparations that must be kept stable for several weeks or months following defrosting, a chaotropic agent corresponding to the definition provided here is used in a lower concentration to avoid the aggregation of fibrinogen, and that the concentration of inorganic salts is reduced and that, if necessary, an antifibrinolytic as well as other common additives and buffer substances are used. A fibrinogen preparation used for this purpose can also contain Factor XIII from the starter material as well as other plasma proteins, such as fibronectin and von Willebrand-Factor (vWF), or it can contain purified Factor XIII as an additive.

Aprotinin, lysine, $\epsilon$-amino caproic acid (EACA), or p-aminomethylbenzoic acid (PAMBA) or their physiologically safe salts can be used as an antifibrinolytic. Studies on the influence of various antifibrinolytics have surprisingly shown that lysine, PAMBA or EACA do not have a negative effect on the activity of Factor XIII, while tranexaminic acid (AMCA) does. Therefore, with frozen fibrinogen/Factor XIII mixtures and also with fibrinogen/Factor XIII mixtures stored in liquid state, EACA or lysine can be used in place of AMCA. Other stabilizers can be used for Factor XIII, such as sodium citrate, amino acids and sugar.

Instead of the aforementioned protein preparations, which comprise Factor XIII as well as fibrinogen and their respective stabilizers, it is also possible to store both concentrations separately and only mix them with the thrombin-containing preparation immediately prior to using them as tissue glue. Therefore, another embodiment of the invention relates to a tissue glue that is comprised of a solution that contains the stabilized Factor XIII, a solution that contains the stabilized fibrinogen, and a solution that contains stabilized thrombin, which are provided separately in one packaging unit prepared to be used together. Another advantage of this is that the ratio of Factor XIII and fibrinogen can be changed and adapted to the specific situation as needed.

Preclinical or clinical uses of tissue glues for avoiding adhesion after surgical intervention have also been described in the past with varying success. Thus, H. Moro et al. reported inhibition of pericardial adhesions in a dog model (H. Moro, J. Hayashi, H. Ohzeki, T. Nakayama, O. Namura, K. Hanzawa and N. Yagi. Jap J Thor Cardiovasc Surg 47: 79-84,1999). H. Takeuchi et al. and P.A. De Iaco et al. also describe the successful use of tissue glues for avoiding or reducing adhesions on the horn of the rabbit uterus (H. Takeuchi, Y. Toyonari, N. Mitsuhashi and Y. Kuwabara. J Obstet Gynaecol 23: 479-484,1997; P.A. De Iaco, A. Costa, G. Mazzoleni, G. Pasquinelli, L.

Bassein and A. Marabini. Fertil Steril 62: 400-404, 1994). The reduction in peritoneal adhesions has likewise been described by S. Lindenberg et al. on use of tissue glues in a rat model (S. Lindenberg and J. G. Lauritsen. Annales Chirurgiae and Gynecologiae 73: 11-13, 1984). However, there have also been other authors who observe no reduction in adhesions on use of fibrin glues by comparison with an untreated control.

These were, inter alia, J. F. H. Gauwerki, J. Mann and G. Bastert, Arch Gynt~kol Obstet 247: 161 (1990) and V. A. C. Evrard, A. De Bellis, W. Boeckx and I. A. Brosens, Hum Reprodt 11: 1877-1880 (1996). The reports, which are partly contradictory, can probably be attributed to the fact that the antiadhesive effect which can be achieved with the products available is insufficiently large or leads consistently to ambiguous results.

Very recently, the possibility of using fibrin layers for avoiding adhesions has also been mentioned in the patent literature. International patent application WO 96/22115 describes a sheet-like material consisting of crosslinked fibrin employed for preventing adhesions but not itself having hemostatic properties. In another embodiment, this material is produced in situ and used as a second tissue glue layer without hemostatic properties on top of a first tissue glue with hemostatic activity. However, these methods are either impractical, because the fixing of such a fibrin film is difficult, or laborious, because two tissue glues must be employed in order to achieve both hemostatic activity and antiadhesive properties.

In addition, a preparation of fibrin or fibrinogen and a biocompatible or biodegradable polymer, which forms a viscous solution and has antiadhesive properties, is disclosed in international patent application WO 92/22312.

Therefore, another object of the present invention was to develop a tissue glue which, while having good hemostatic properties, shows improved results in reducing or preventing tissue adhesions and, moreover, does so without addition of polymers, which form viscous solutions and have antiadhesive properties.

Because of their great medical importance, considerable research has been directed in recent years to the further development and improvement of known tissue glues. This has also involved particular attention being paid to the improvement of the storability of tissue glues. Thus, German patent applications DE-A-198 53 033, DE-A-198 61 158 and DE-A 100 12 732 describe tissue glues and components thereof which are distinguished, inter alia, by particularly long storability in the liquid and/or frozen state. German patent application DE-A 100 12 732 is hereby incorporated by reference. Detailed investigation of these novel tissue glues has now shown that they also have other advantageous properties which open up additional and valuable possible uses thereof.

For example, it has emerged that these novel tissue glues have considerably improved antiadhesive properties without involving the need to accept losses of their hemostatic properties. The antiadhesive properties of the novel tissue glues are evident both on untreated wounds and on wounds treated with conventional tissue glues. In this context, the skilled artisan would understand that a conventional tissue glue is a hemostatic tissue glue that either does not have antiadhesive properties or if it does, they are inadequate to perform antiadhesion. It is particularly surprising in this connection that distinctly improved effects, by comparison with conventional tissue glues, in reducing or preventing tissue adhesions is also achieved when the aforementioned novel tissue glues are employed. These effects have been observed both in a typical animal model for investigating the reduction in adhesions, such as a lengthwise incision wound on the horn of the rabbit uterus, and on hemostatic use in a partial resection of the rabbit liver.

In one embodiment, the invention therefore relates to the use of a tissue glue comprising:
   a stabilized fibrinogen preparation, which can be stored in the liquid and/or frozen state and to which a chaotropic substance is added, and
   a thrombin preparation for reducing or preventing postoperative tissue adhesions.

It is also possible to add to the tissue glue a preparation containing coagulation Factor XIII if the latter is not present in sufficient quantity, so that it is used as 3-component glue. This is because fibrin crosslinking, which should be as complete as possible, can enhance the antiadhesive effect of a fibrin glue by the fibrin matrix being, for example, less amenable to fibrinolytic degradation. However, it is also possible to admix coagulation Factor XIII to the fibrinogen preparation from the outset, so that a 2-component glue is employed. In the case of a 3-component glue, the mixing ratio of the components fibrinogen, Factor XIII and thrombin can be chosen in a suitable way in order to achieve good mechanical properties of the glue. Examples of suitable mixing ratios include about 1:1:1 to about 10:1:1 or 10:1:2 or, in general, x:y:z where $x \geq z \geq y$.

As mentioned previously, the tissue glue used according to the invention comprises a chaotropic substance in the fibrinogen preparation. Examples of chaotropic substances that have proved suitable include arginine, guanidine, citrulline, urea and their derivatives or mixtures thereof. Chaotropic substances are generally added to the fibrinogen preparation in amounts of from about 0.1 to about 1.0 mol/l, for example in amounts of less than 0.5 mol/l.

In another embodiment of the invention, the properties of the aforementioned novel tissue glues are further advantageously influenced by addition of an antifibrinolytic agent. Examples of antifibrinolytic agents include aprotinin, c-aminocaproic acid (EACA), p-aminomethylbenzoic acid (PAMBA) or one of their physiologically tolerated salts or derivatives.

The fibrinogen preparation may additionally comprise as stabilizers:
an inorganic salt or
one or more physiologically tolerated salts of organic carboxylic acids, for example, citric acid or of lactic acid, or
one or more amino acids or
a mono- or disaccharide or
a sugar alcohol or one of their mixtures.

In another embodiment of the invention, a beneficial effect on the antiadhesive properties of the claimed, improved fibrin glues can further be achieved by suitable purification methods, for example by reducing the plasminogen content of the fibrinogen component. Examples of possible methods of this type are immunoaffinity chromatography via coupled antibodies or affinity chromatography on amino group-containing supports. This invention therefore also encompasses, inter alia, fibrin glues with fibrinogen components whose plasminogen contents have been significantly reduced. For example, fibrinogen components may have a plasminogen to fibrinogen ratio of less than $1.8 \times 10^{-4}$ (w/w), including less than $10^{-4}$ (w/w).

The Factor XIII preparation added to the tissue glue to be employed according to the invention may likewise be stabilized if it is not added to the previously stabilized fibrinogen. Therefore, in one embodiment of the invention, it may be advantageous to add to the Factor XIII preparation a stabilizer, for example, a physiologically tolerated salt of an organic di-, tri- or tetracarboxylic acid, such as citric acid, and, where appropriate, other stabilizers and/or buffer substances for Factor XIII.

Other stabilizers suitable in this connection include:
a mono- or disaccharide or a sugar alcohol and/or
one or more amino acids chosen from the group of glycine, glycylglycine, alanine, cysteine, histidine, glutamine or a physiologically tolerated salt of glutamic or aspartic acid and/or
a reducing or oxidation-preventing agent and/or
a surface-active substance.

Stabilizers are normally added in an amount of up to about 5% by weight of the Factor XIII preparation. Tissue glues of this type are described in German patent applications DE-A-198 53 033 and DE-A-198 61 158.

In another embodiment of the invention, the thrombin preparation present in the tissue glue employed according to the invention may contain a non-covalently binding inhibitor as stabilizer. Suitable substances for this purpose include, for example, compounds such as benzamidine or p-aminobenzamidine and other low to moderate affinity protease inhibitors. The addition of these low or moderate affinity inhibitors negligibly impairs the activity of thrombin in relation to substances such as fibrinogen. It is additionally possible, for stabilization purposes, to add to the thrombin preparation, besides a soluble calcium salt, sodium chloride, a sugar or a sugar alcohol and/or an amino acid or else the salt of a mono- or polycarboxylic acid and/or the salt of a mono- or polyhydroxy carboxylic acid or mixtures of said stabilizers.

The thrombin used for this purpose is prepared from the prothrombin obtained from plasma or from a plasma fraction. After an activation thereof to thrombin without addition of thromboplastin and, where appropriate, further processing steps, thrombin can be purified by a hydrophobic interaction chromatography and/or a cation exchange chromatography. This method is described in detail in German patent application DE-A-100 12 732.

In another embodiment of the invention, it may be advantageous in this connection for the tissue glue or its constituents also to be subjected to one or more methods for inactivating viruses.

It is possible to use as starting material for producing the individual components of the fibrin glue of the invention, apart from plasma fractions, recombinant proteins prepared by isolation from cell cultures or cell culture supernatants.

EXAMPLES

A) Frozen or Lyophilized Concentrates that can be Stored in Liquid State for Several Weeks/Months at 0 to 10° Celsius (See Table 1)

Stable, frozen fibrinogen concentrates are known and have been described, but their stability after defrosting is limited to a few days. The limited stability of the fibrinogen concentrate is, among other things, also attributable to the fact that the viscosity soon increases due to the aggregation of the fibrinogen. It is possible to obtain a low viscosity in the liquid state by adding compounds that prevent aggregation, i.e., chaotropic compounds, but these agents have the disadvantage that they lead to a drop in the Factor XIII-activity in frozen state (for example, at −20° Celsius). Generally, the loss of Factor XIII-activity occurs in proportion to the concentration of chaotropic agents, i.e., the higher the concentration of chaotropic agents, the quicker the loss of Factor XIII activity.

In the development of the stabilized protein preparations in accordance with the invention, it was now found that not all chaotropic agents have the same influence on the stability of the Factor XIII, and that the other additives to be added in accordance with the invention also have a significant influence on the Factor XIII stability and on the viscosity affected by the fibrinogen aggregation. For example, at the same molarity, arginine is significantly more effective in the prevention of fibrinogen polymerization or aggregation than urea. Furthermore, anti-fibrinolytic additives such as the E-amino caproic acid (EACA), p-aminomethylcyclohexanecarboxylic acid (AMCA) or p-aminomethylbenzoic acid (PAMBA) as well as their physiologically safe salts have an effect on fibrinogen aggregation and Factor XIII stability. AMCA, for example, has a negative effect on Factor III-activity at storage in frozen state. Surprisingly, EACA, which has a chemical structure very similar to that of AMCA, does not cause the same Factor XIII-drop as AMCA under appropriate conditions. It was further found that Factor XIII-activity in frozen protein concentrates is not reduced in the presence of specific concentrations of chaotropic agents when the addition of inorganic salts, which until now was common in preparations of this type, is abandoned or limited as much as possible. Thus, in the preparation developed in accordance with the invention, fibrinogen and Factor XIII remain liquid and the activity is maintained for at least several weeks or even months after freezing and defrosting, if said formulation comprises a chaotropic compound in a quantity of less than 0.28 mol/liter of a substance that avoids or reduces the aggregation of fibrinogen. For example, arginine may be used in a quantity of approximately 2 percent by weight. Other slightly chaotropic agents such as citrulline, nicotine amide, urea, etc. or mixtures thereof, for example with arginine, can be used in a quantity of up to 0.28 M, for instance in the range of about 0.1 to 0.20 M. Furthermore, it is also possible to add water-soluble inorganic salts in concentrations of $\leq 100$ mmol/liter, including $\leq 50$ mmol/liter, and $\leq 20$ mmol/liter, in addition to the anti-fibrinolytic compound.

In one of the preparations in accordance with the invention, the fibrinogen as well as Factor XIII remain stable for at least several weeks or months during storage in frozen as well as in liquid state. The addition of other components, such as salts of citric acid or lactic acid or one or several amino acids or a mono- or disaccharide or a sugar alcohol or one of their mixtures can also favorably influence the stability. With these compositions, the preparation can be refrozen and defrosted or refrozen after reconstitution of a fibrin glue lyophilizate and stored in frozen condition as a stable fibrinogen/Factor XIII preparation. This is a further advantage of the formulations in accordance with the invention because refreezing is not possible with the commercial frozen or lyophilized protein preparations that are used as tissue glues. This property simplifies the handling of lyophilizates after the reconstitution, or of frozen stored preparations if the entire quantity is not used in one process.

The following examples explain the production of fibrinogen-, fibrinogen/Factor XIII- or Factor XIII-concentrates to examine the stability of various formulations. It is also possible, for example, to use fibrinogen, Factor XIII or thrombin from transgenic or recombinant production as starter materials:

Example 1

A fibrinogen concentrate was prepared from cryoprecipitate through precipitation, $Al(OH)_3$-adsorption, virus inactivation, and further precipitation (see P. Fuhge, P. Gratz, H. Geiger. "Moderne Methoden für die Herstellung von Gerinnungstherapeutika. (Modern methods for the preparation of coagulation therapeutics). Behring Inst. Mitt. 79:164-176 (1986)). Various chemical or physical processes can be used to inactivate or remove a virus. Said processes are effective for coated or non-coated viruses. The fibrinogen concentrate was adjusted to the respective composition as well as to a final fibrinogen concentration of more than 15 mg/ml, for example, more than 60 mg/ml, with diafiltration and subsequent concentration. The stability of these fibrinogen preparations was determined in the presence of 0.05% sodium azide and stored at the respective temperature and testing of the relevant analysis parameters such as coagulatable fibrinogen, Factor XIII-activity, viscosity, protein breakdown through SDS-PAGE, etc.

Example 2

Purified Factor XIII was prepared from a plasma fraction containing Factor XIII (Cohn-Fraction I) (H. E. Karges and R. Rapp: Production and virus safety of human Factor XIII concentrates. In: Factor XIII, eds. J. McDonagh, R. Seitz, R. Egbring, Schattauer, Stuttgart/New York, pp. 66-76 (1993)). After dialysis or diafiltration and, if necessary, ultrafiltration, this Factor XIII-solution was mixed with the stabilizers to be tested and stored at various temperatures after sterile filtration, or used as standard addition for fibrinogen concentrates.

Example 3

As in Example 1, a fibrinogen concentration was prepared and the Factor XIII-content was topped off by adding a Factor XIII-solution. The preparations used for the stability analysis were prepared by subsequent dialysis and concentration to approximately 60 mg/ml fibrinogen and higher as well as 10 E/ml Factor XIII and higher. To prevent the growth of bacteria, the batches also contained 0.05% sodium azide or were filtered sterile with filters of 0.2 µm pore size.

Example 4

The lyophilized fibrinogen concentrate of a commercial fibrin glue (Beriplast P) was reconstituted in water for injection purposes or in aprotinin solution to a fibrinogen strength of >15 mg/ml, for example, to >60 mg/ml, and dialyzed against mixtures with various additives. The fibrinogen/Factor XIII-concentrates were stored in the presence of 0.05% $NaN_3$ to avoid the growth of bacteria and their stability was analyzed at various times.

Example 5

A fibrinogen concentrate was prepared from cryoprecipitate with subsequent $AL(OH)_3$-adsorption and inactivation of the virus, and the Factor XIII-concentration of said fibrinogen concentrate was topped off with the addition of purified Factor XIII, if necessary. This concentration was adjusted to the respective composition as well as to a final fibrinogen concentration of more than 15 mg/ml, for example, more than 40 mg/ml, by diafiltration and subsequent concentration. To test the storage stability, it was stored in the presence of 0.05% sodium azide.

Example 6

Fibrinogen-/Factor XIII-concentrations were prepared according to the aforementioned examples and dialyzed and lyophilized against various formulation buffers. The resulting lyophilizates were tested directly for stability, or the solutions obtained after reconstitution were stored at temperatures of 0-10° Celsius and their stability was reviewed as indicated.

The stability of fibrinogen-, Factor XIII- as well as fibrinogen-Factor XIII-preparations prepared according to one of the examples 1-6 was determined by storage at the respective temperature and by testing the relevant analysis parameters. The results of these tests are listed in Tables 1 to 3. Generally, however, there are also other appropriate methods known in the art for the production of fibrinogen or Factor XIII, which can comprise other purification steps.

B) Concentrates Stored in Liquid State, Containing Fibrinogen- or Fibrinogen/Factor XIII-Concentrate (See Tables 1 and 2)

Even with liquid fibrinogen- or fibrinogen/Factor XIII-concentrates that are not frozen but are stored only in refrigerated state around 0 to 10° Celsius, the aggregation and thus the increase in viscosity must be controlled with the addition of chaotropic agents. This generally leads to a more or less severe drop in the activity of Factor XIII (compare Table 1, Batch 4 and 5). We have now found that the increase in viscosity can be prevented or reduced and that the drop in Factor XIII can be decreased if the chaotropic substance is used in a quantity of less than about 0.28 mol/liter. Arginine, guanidine, citrulline, nicotine amide and their mixtures have proven to be suitable chaotropic substances if they are employed in the aforementioned quantity. In another embodiment of the invention, it may be further advantageous to add an anti-fibrinolytic such as aprotinin, lysine, ε-amino caproic acid (EACA), p-aminomethylbenzoic acid (PAMBA) or one of their physiologically safe salts or derivatives to the preparation, as well as physiologically safe salts of organic carboxylic acids, such as citric acid or lactic acid and, if necessary, one or more amino acids or a mono- or disaccharide or sugar alcohol as a further stabilizer of the fibrinogen- or fibrinogen-/Factor XIII-preparation. In this way, it is possible to obtain improved stabilities in fibrinogen concentrates with a fibrinogen strength of more than 15 mg/ml, including more than 60 mg/ml, when using chaotropic agents in a quantity of up to 0.28 M.

If mixtures of fibrinogen and Factor XIII are prepared, the simultaneous presence of chaotropic agents and the aforementioned additives or mixtures guarantee that the preparations reach improved stability values for fibrinogen as well as for Factor XIII in comparison to the known formulations. This mixture of fibrinogen and Factor XIII can be provided in combination with a preparation that contains thrombin to be used together as a tissue glue in one packaging unit designed for this purpose.

C) Liquid Concentrates with Separate Storage of Fibrinogen and Factor XIII (See Tables 1-3)

It was shown that the stability of a liquid preparation comprising fibrinogen and Factor XIII could be further improved if fibrinogen and Factor XIII were stored separately and were not mixed together until immediately prior to or during the application. In that case, the Factor XIII-concentrate is stabilized independently of the fibrinogen. It has been shown that the Factor XIII preparation, which in one embodiment of the invention is essentially fibrinogen-free, can be stabilized with the addition of a physiologically safe salt of an organic di- or tri-carboxylic acid, such as citric acid, and the addition of further common stabilizers for Factor XIII in a quantity of up to 10 percent by weight, for example up to 5 percent by weight, as well as mixtures thereof, for storage in liquid state at 0 to 10° Celsius or 20 to 25° Celsius (see Table 3). Mono- or disaccharides or sugar alcohols and amino acids from the group of glycine, glycylglycine, alanine, cysteine, histidine, glutamine or physiologically safe salts of the glutamine acid or the asparagine acid or mixtures thereof may be used as common stabilizers for Factor XIII. Furthermore, it is possible to add additives to control osmolarity, the pH-value, or other common stabilizers for Factor XIII, if necessary. The fibrinogen concentrate is stabilized as mentioned above.

The separate storage of Factor XIII- and fibrinogen preparations at 0 to 10° Celsius, which has respective stabilizers, allows the production of a fibrin glue that is comprised of three stable liquid components, i.e., the fibrinogen concentrate, Factor XIII-concentrate, and the thrombin concentrate. In this form, the components remain stable over a long time and retain their activity until they are mixed together immediately prior to or during the application as tissue glue. The formulations stated here also allow a freezing of the individual components without any significant loss of activity.

The Factor XIII and fibrinogen preparations stabilized in accordance with the invention can also be used parenterally or topically as independent components for therapeutic purposes.

Examples of Formulations Comprising Fibrinogen and/or Factor XIII

Formulations analogous to the state of the art:
1. 0.1 mol/liter NaCl, 3 grams/liter $Na_3$-citrate$\times 2H_2O$, 8 grams/liter glycine, 0.09 mol/liter L-arginine, 0.58 mol/liter AMCA, pH 7.4
2. 6 grams/liter $Na_3$-citrate$\times 2H_2O$, 1% glycine, 2% nicotine amide, 1,000 KIE/ml aprotinin, pH 7.5
3. 1.8 grams/liter $Na_3$-citrate$\times 2H_2O$, 16.3 grams/liter glycine, 0.36 grams/liter triton, 8.1 grams/liter HSA, 0.2 mol/liter nicotine amide, pH 7.3
4. 0.15 mol/liter NaCl, 0.29 mol/liter L-arginine, 1,000 KIE/ml aprotinin, pH 7.0
5. 0.15 mol/liter NaCl, 0.5 mol/liter urea, 1,000 KIE/ml aprotinin, pH 7.0

Formulations made in accordance with the invention as well as comparative batches comprising fibrinogen or fibrinogen/Factor XIII:
6. 6 grams/liter $Na_3$-citrate$\times 2H_2O$, 0.12 mol/liter L-arginine, pH 7.4
7. 6 grams/liter $Na_3$-citrate$\times 2H_2O$, 0.12 mol/liter L-arginine, 0.14 mol/liter citrulline, pH 7.4
8. 6 grams/liter $Na_3$-citrate$\times 2H_2O$, 0.095 mol/liter L-arginine, 80 mmol/liter EACA, pH 7.4
9. 6 grams/liter $Na_3$-citrate$\times 2H_2O$, 0.12 mol/liter L-arginine, 0.14 mmol/liter citrulline, 80 mmol/liter EACA, pH 7.4
10. 6 grams/liter $Na_3$-citrate$\times 2H_2O$, 0.12 mol/liter L-arginine, 80 mmol/liter EACA, pH 7.4*

*Batch prepared by reconstituting the appropriate lyophilizate with water for injection purposes.

11. 0.1 mol/liter NaCl, 6 grams/liter $Na_3$-citrate$\times 2H_2O$, 0.24 mol/liter L-arginine, 80 mmol/liter EACA, pH 7.4
12. 0.1 mol/liter NaCl, 6 grams/liter $Na_3$-citrate$\times 2H_2O$, 0.24 mol/liter L-arginine, 320 mmol/liter L-lysine, pH 7.4
13. 6 mg/ml $Na_3$-citrate$\times 2H_2O$, 0.12 mol/liter L-arginine, 0.14 mol/liter citrulline, 80 mmol/liter EACA, pH 7.4
14. 3 grams/liter $Na_3$-citrate$\times 2H_2O$, 0.24 mol/liter L-arginine, 80 mmol/liter EACA, pH 7.0
15. 0.15 M NaCl, 6 grams/liter $Na_3$-citrate$\times 2H_2O$, 0.24 mol/liter L-arginine, 1,000 KIE/ml aprotinin, pH 7.0
16. 6 grams/liter $Na_3$-citrate$\times 2H_2O$, 0.24 mol/liter L-arginine$\times$HCl, 80 mmol/liter EACA, pH 7.5
17. 6 grams/liter $Na_3$-citrate$\times 2H_2O$, 0.24 mol/liter L-arginine$\times$HCl, 80 mmol/liter PAMBA, pH 7.2
18. 6 grams/liter $Na_3$-citrate$\times 2H_2O$, 0.24 mol/liter L-arginine$\times$HCl, 8% mannitol, 80 mmol/liter EACA, pH 7.5
19. 6 grams/liter $Na_3$-citrate$\times 2H_2O$, 0.15 M NaCl, 2% nicotine amide, 1,000 KIE/ml aprotinin, pH 7.5
20. 0.15 mol/liter NaCl, 6 grams/liter $Na_3$-citrate$\times 2H_2O$, 0.24 mol/liter L-arginine, 320 mmol/liter lysine, pH 7.5
21. 0.15 mol/liter NaCl, 6 grams/liter $Na_3$-citrate$\times 2H_2O$, 0.24 mol/liter L-arginine, 80 mmol/liter EACA, pH 7.5
22. 6 grams/liter $Na_3$-citrate$\times 2H_2O$, 0.24 mol/liter L-arginine, 320 mmol/liter lysine, 7.0

23. 6 grams/liter $Na_3$-citrate×$2H_2O$, 0.24 mol/liter L-arginine, 80 mmol/liter EACA, pH 7.0
24. 0.15 mol/liter NaCl, 6 grams/liter $Na_3$-citrate×$2H_2O$, 0.24 mol/liter L-arginine, 2% L-histidine, 1,000 KIE/ml aprotinin, pH 7.5
25. 0.15 mol/liter NaCl, 6 grams/liter $Na_3$-citrate×$2H_2O$, 0.24 mol/liter L-arginine, 2% sucrose, 1,000 KIE/ml aprotinin, pH 7.5

Formulations made in accordance with the invention, comprising Factor XIII as independent component 26. 1.5 grams/liter $Na_3$-citrate×$2H_2O$, 2.9 grams/liter NaCl, 3 grams/liter L-arginine×HCl, pH 7.4
27. 6 grams/liter $Na_3$-citrate×$2H_2O$, pH 7.4
28. 1.5 grams/liter $Na_3$-citrate×$2H_2O$, 2.9 grams/liter NaCl, pH 7.4
29. 3 grams/liter $Na_3$-citrate×$2H_2O$, 1% glycine, pH 7.4
30. 3 grams/liter $Na_3$-citrate×$2H_2O$, 2% mannitol, 10 mmol/liter L-histidine, pH 7.4
31. 6 grams/liter $Na_3$-citrate×$2H_2O$, 2% mannitol, pH 7.4
32. 6 grams/liter $Na_3$-citrate×$2H_2O$, 1% HSA, pH 7.4
33. 5 mmol/liter EDTA, 50 mmol/liter trismethylamine ×HCl, pH 7.4
34. 6 grams/liter $Na_3$-citrate×$2H_2O$, 1% L-histidine, pH 7.4
35. 1.5 grams/liter $Na_3$-citrate×$2H_2O$, 2.92 grams/liter NaCl, 50 mmol/liter glycylglycine, pH 7.4
36. 3 grams/liter $Na_3$-citrate×$2H_2O$, 1% L-histidine, pH 7.4
37. 3 grams/liter $Na_3$-citrate×$2H_2O$, 38 mmol/liter glycylglycine, pH 7.4

In general, batch numbers 1-37 in Tables 1-3 refer to the formulation numbers 1-37 in the preceding section.

TABLE 1a

Stability of fibrinogen or fibrinogen/Factor XIII in various formulations at 4° Celsius

| Storage time | Batch | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |

Evaluation of viscosity (storage temperature: 4° Celsius): 1 = low viscosity, 2 = medium viscosity, 3 = high viscosity, 4 = solid at 4° Celsius. In all of the following tables, the storage time is stated in months:

| 0 | 1 | 1 | 1 | 1 | 1 | 1 | 1 | 1 | 1 | 1 | 1 | 1 | 1 |
|---|---|---|---|---|---|---|---|---|---|---|---|---|---|
| 0.5 | 1 | 1 | nd | 1 | 1 | 1 | 1 | 1 | 1 | nd | 1 | 1 | 1 |
| 1 | 1 | 2 | 2 | 1 | 1 | 1 | 1 | 1 | 1 | 1 | 1 | 1 | 1 |
| 3 | 2 | 3 | 3 | 1 | 1 | 1 | 1 | 1 | 1 | 1 | 1 | 1 | 1 |
| 6 | 2 | 4 | 3 | 1 | 1 | 1 | 1 | | 1 | 1 | 1 | 1 | 1 |
| 9 | 3 | nd | 3 | 1 | 1 | 1 | 1 | | 1 | | | | 1 |
| 12 | 3 | nd | | 1 | 1 | 1 | 1 | | 1 | | | | 1 |

Fibrinogen (% of zero value), storage temperature: 4° Celsius

| 0 | 100 | 100 | 100 | 100 | 100 | 100 | 100 | 100 | 100 | 100 | 100 | 100 | 100 |
|---|---|---|---|---|---|---|---|---|---|---|---|---|---|
| 0.5 | 103 | 98 | nd | 106 | 100 | 97 | 94 | 105 | 91 | nd | 104 | 95 | 91 |
| 1 | 99 | 94 | 98 | 110 | 97 | 92 | 91 | 109 | 95 | 102 | 109 | 103 | 95 |
| 3 | 99 | (96) | (100) | 111 | 98 | 89 | 92 | 104 | 91 | 103 | 108 | 99 | 91 |
| 6 | 100 | (100) | (90) | 97 | 98 | 92 | 87 | | 91 | 87 | 94 | 100 | 91 |
| 9 | (96) | nd | (81) | 98 | 84 | 80 | 80 | | 86 | | | | 86 |
| 12 | (103) | nd | | 93 | 89 | 80 | 75 | | 90 | | | | 90 |

Factor XIII (% of zero value); storage temperature: 4° Celsius

| 0 | 100 | 100 | 100 | 100 | 100 | 100 | 100 | 100 | 100 | 100 | | | 100 |
|---|---|---|---|---|---|---|---|---|---|---|---|---|---|
| 0.5 | 101 | 93 | nd | 73 | 81 | 98 | 100 | 100 | 102 | nd | | | 102 |
| 1 | 105 | 87 | 97 | 73 | 81 | 100 | 97 | 97 | 100 | 93 | | | 100 |
| 3 | 100 | (80) | (89) | 63 | 77 | 95 | 93 | 100 | 95 | 93 | | | 95 |
| 6 | 89 | (83) | (80) | 49 | 67 | 102 | 95 | | 95 | 83 | | | 95 |
| 9 | (98) | nd | (78) | 42 | 65 | 92 | 80 | | 86 | | | | 86 |
| 12 | (89) | nd | | 39 | 69 | 83 | 92 | | 85 | | | | 85 |

TABLE 1b

Stability of fibrinogen or fibrinogen/Factor XIII in various formulations at −20° Celsius

| Storage time | Batch | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |

Evaluation of viscosity after defrosting (storage temperatures: −20° Celsius); 1 = low viscosity, 2 = medium viscosity, 3 = high viscosity, 4 = solid at 4° Celsius

| 0 | 1 | 1 | 1 | nd | nd | 1 | 1 | 1 | 1 | nd | nd | nd | 1 |
|---|---|---|---|---|---|---|---|---|---|---|---|---|---|
| 0.5 | 1 | 1 | nd | nd | nd | 1 | 1 | 1 | 1 | nd | nd | nd | 1 |
| 1 | 1 | 1 | 1 | nd | nd | 1 | 1 | 1 | 1 | nd | nd | nd | 1 |

TABLE 1b-continued

Stability of fibrinogen or fibrinogen/Factor XIII in various formulations at −20° Celsius

| Storage time | Batch | | | | | | | | | | | | |
|---|---|---|---|---|---|---|---|---|---|---|---|---|---|
| | 1 | 2 | 3 | 4 | 5 | 6 | 7 | 8 | 9 | 10 | 11 | 12 | 13 |
| 3 | 1 | 1 | 1 | nd | nd | 1 | 1 | 1 | 1 | nd | nd | nd | 1 |
| 6 | 1 | 1 | 1 | nd | nd | 1 | 1 | 1 | 1 | nd | nd | nd | 1 |
| 9 | 1 | 1 | 1 | nd | nd | 1 | 1 | 1 | 1 | | | | 1 |
| 12 | 1 | 1 | | nd | nd | 1 | 1 | 1 | 1 | | | | 1 |
| Fibrinogen (% of zero value); storage temperature: −20° Celsius | | | | | | | | | | | | | |
| 0 | 100 | 100 | 100 | nd | nd | 100 | 100 | 100 | 100 | nd | nd | nd | 100 |
| 0.5 | 96 | 101 | nd | nd | nd | nd | 99 | 100 | 99 | nd | nd | nd | 99 |
| 1 | 100 | 95 | 95 | nd | nd | 99 | 100 | 101 | 93 | nd | nd | nd | 93 |
| 3 | 99 | 100 | 100 | nd | nd | 99 | 103 | 114 | 101 | nd | nd | nd | 101 |
| 6 | 99 | 101 | 105 | nd | nd | 100 | 106 | 115 | 103 | nd | nd | nd | 103 |
| 9 | 89 | nd | 108 | nd | nd | 93 | 104 | 100 | 94 | | | | 94 |
| 12 | 87 | nd | | nd | nd | 100 | 95 | 100 | 99 | | | | 99 |
| Factor XIII (% of zero value); storage temperature: −20° Celsius | | | | | | | | | | | | | |
| 0 | 100 | 100 | 100 | nd | nd | 100 | 100 | 100 | 100 | nd | nd | nd | 100 |
| 0.5 | 57 | 30 | nd | nd | nd | nd | 98 | 108 | 102 | nd | nd | nd | 102 |
| 1 | 48 | 8 | 15 | nd | nd | 100 | 102 | 102 | 95 | nd | nd | nd | 95 |
| 3 | 35 | 5 | 10 | nd | nd | 98 | 94 | 107 | 98 | nd | nd | nd | 98 |
| 6 | 24 | 5 | 15 | nd | nd | 107 | 98 | 102 | 97 | nd | nd | nd | 97 |
| 9 | 14 | nd | 10 | nd | nd | 95 | 100 | 102 | 93 | | | | 93 |
| 12 | 1 | nd | | nd | nd | 97 | 95 | 108 | 98 | | | | 98 |

TABLE 2a

Stability of fibrinogen or fibrinogen/Factor XIII in various formulations at 4° Celsius

| Storage time | 14 | 15 | 16 | 17 | 18 | 19 | 20 | 21 | 22 | 23 | 24 | 25 |
|---|---|---|---|---|---|---|---|---|---|---|---|---|
| Evaluation of viscosity after defrosting (storage temperature 4° Celsius); 1 = low viscosity, 2 = medium viscosity, 3 = high viscosity, 4 = solid at 4° Celsius | | | | | | | | | | | | |
| 0 | 1 | 1 | 1 | 1 | 1 | 1 | 1 | 1 | 1 | 1 | 1 | 1 |
| 0.5 | 1 | 1 | 1 | 1 | 1 | 1 | 1 | 1 | 1 | 1 | 1 | 1 |
| 1 | 1 | 1 | 1 | 1 | 1 | 1 | 1 | 1 | 1 | 1 | 1 | 1 |
| 3 | 1 | 1 | 1 | 1 | 1 | 1 | 1 | 1 | 1 | 1 | 1 | 1 |
| 6 | 1 | 1 | 1 | 1 | 1 | 1 | 1 | 1 | 1 | | | 1 |
| 9 | 1 | 1 | 1 | 1 | 1 | 1 | 1 | 1 | 1 | | | 1 |
| 12 | | 1 | 1 | | 1 | 1 | 1 | 1 | | | | |
| Fibrinogen (% of zero value), storage temperature: 4° Celsius | | | | | | | | | | | | |
| 0 | 100 | 100 | 100 | 100 | 100 | 100 | 100 | 100 | 100 | 100 | 100 | 100 |
| 0.5 | 100 | 93 | 98 | nd | 98 | 99 | 94 | 91 | 92 | 96 | 97 | 101 |
| 1 | 95 | 93 | 95 | 99 | 102 | 91 | 101 | 94 | 91 | 94 | 96 | 96 |
| 3 | 84 | 87 | 90 | 105 | 112 | 99 | 98 | 86 | 89 | 94 | 83 | 94 |
| 6 | 97 | 79 | 96 | 108 | 118 | 101 | 92 | 82 | 90 | 102 | | 87 |
| 9 | 95 | 88 | 89 | 94 | 112 | 109 | 98 | 88 | 96 | 97 | | |
| 12 | | 77 | 82 | | 96 | 94 | 86 | 78 | | | | |
| Factor XIII (% of zero value), storage temperature: 4° Celsius | | | | | | | | | | | | |
| 0 | | | | 100 | 100 | | | | | | 100 | 100 |
| 0.5 | | | | nd | 93 | | | | | | 96 | 93 |
| 1 | | | | 100 | 83 | | | | | | 84 | 86 |
| 3 | | | | 82 | 80 | | | | | | 71 | 76 |
| 6 | | | | 91 | 77 | | | | | | | 67 |
| 9 | | | | 91 | 80 | | | | | | | |
| 12 | | | | | 77 | | | | | | | |

TABLE 2b

Stability of fibrinogen or fibrinogen/Factor XIII in various formulations at −20° Celsius

| Storage time | 14 | 15 | 16 | 17 | 18 | 19 | 20 | 21 | 22 | 23 | 24 | 25 |
|---|---|---|---|---|---|---|---|---|---|---|---|---|
| Evaluation of viscosity after defrosting (storage temperature: 20° Celsius); 1 = low viscosity, 2 = medium viscosity, 3 = high viscosity, 4 = solid at 4° Celsius | | | | | | | | | | | | |
| 0 | nd | 1 | 1 | nd | 1 | 1 | 1 | 1 | nd | nd | 1 | 1 |
| 0.5 | nd | 1 | 1 | nd | 1 | 1 | 1 | 1 | nd | nd | 1 | 1 |
| 1 | nd | 1 | 1 | nd | 1 | 1 | 1 | 1 | nd | nd | 1 | 1 |
| 3 | nd | 1 | 1 | nd | 1 | 1 | 1 | 1 | nd | nd | 1 | 1 |
| 6 | nd | 1 | 1 | nd | 1 | 1 | 1 | 1 | nd | nd |  | 1 |
| 9 | nd | 1 | 1 | nd | 1 | 1 | 1 | 1 | nd | nd |  |  |
| 12 | nd | 1 | 1 | nd | 1 | 1 | 1 | 1 | nd | nd |  |  |
| Fibrinogen (% of zero value), storage temperature: −20° Celsius | | | | | | | | | | | | |
| 0 | nd | 100 | 100 | nd | 100 | 100 | 100 | 100 | nd | nd | 100 | 100 |
| 0.5 | nd | 96 | 100 | nd | 100 | 96 | 91 | 86 | nd | nd | 90 | 94 |
| 1 | nd | 94 | 99 | nd | 98 | 100 | 99 | 93 | nd | nd | 94 | 97 |
| 3 | nd | 85 | 94 | nd | 94 | 92 | 97 | 93 | nd | nd | 85 | 90 |
| 6 | nd | 85 | 98 | nd | 98 | 90 | 99 | 92 | nd | nd |  | 89 |
| 9 | nd | 86 | 95 | nd | 100 | 87 | 91 | 79 | nd | nd |  |  |
| 12 | nd | 84 | 93 | nd | 98 | 87 | 84 | 81 | nd | nd |  |  |

TABLE 3

Stability of Factor XIII in various formulations at 4° Celsius, 20 to 25° Celsius and −20° Celsius Factor XII (% of zero value), storage temperature: 4° Celsius

| Storage time | 26 | 27 | 28 | 29 | 30 | 31 | 32 | 33 | 34 | 35 | 36 | 37 |
|---|---|---|---|---|---|---|---|---|---|---|---|---|
| 0 | 100 | 100 | 100 | 100 | 100 | 100 | 100 | 100 | 100 | 100 | 100 | 100 |
| 0.5 | 90 | 94 | nd | nd | nd | nd | nd | nd | nd | nd | nd | nd |
| 1 | 95 | 94 | 128 | 96 | 114 | 104 | 101 | 76 | 100 | 97 | 116 | 108 |
| 3 | 105 | 101 | 134 | 110 | 113 | 108 | 104 | 114 | 116 | 115 | 116 | 134 |
| 6 | 112 | 102 | 136 | 110 | 105 | 106 | 103 | 106 | 114 | 103 | 103 | 114 |
| 9 | 116 | 112 | 133 | 112 |  | 113 | 106 | 118 | 118 | 113 | 97 | 115 |
| 12 |  |  |  |  |  |  |  |  | 117 | 134 |  |  |

| Storage time | Batch | | | | | | | | | | | |
|---|---|---|---|---|---|---|---|---|---|---|---|---|
|  | 26 | 27 | 28 | 29 | 30 | 31 | 32 | 33 | 34 | 35 | 36 | 37 |
| Factor XIII (% of hundred), storage temperature: −20° Celsius | | | | | | | | | | | | |
| 0 |  | 100 |  |  |  |  |  |  |  |  |  |  |
| 0.5 |  | 92 |  |  |  |  |  |  |  |  |  |  |
| 1 |  | 99 |  |  |  |  |  |  |  |  |  |  |
| 3 |  | 97 |  |  |  |  |  |  |  |  |  |  |
| 6 |  | 106 |  |  |  |  |  |  |  |  |  |  |
| 9 |  | 108 |  |  |  |  |  |  |  |  |  |  |
| 12 |  | 112 |  |  |  |  |  |  |  |  |  |  |

| Storage time | Batch | | | | | | | | | | | |
|---|---|---|---|---|---|---|---|---|---|---|---|---|
|  | 26 | 27 | 28 | 29 | 30 | 31 | 32 | 33 | 34 | 35 | 36 | 37 |
| Factor XIII (% of zero value), storage temperature: 20 to 25° Celsius | | | | | | | | | | | | |
| 0 |  |  |  |  | 100 | 100 | 100 | 100 | 100 | 100 | 100 | 100 |
| 0.5 |  |  |  |  | nd | nd | nd | nd | nd | nd | nd | nd |
| 1 |  |  |  |  | 120 | 105 | 104 | 104 | 109 | 103 | 115 | 119 |
| 3 |  |  |  |  | 111 | 112 | 105 | 113 | 112 | 109 | 108 | 120 |
| 6 |  |  |  |  | 94 | 104 | 99 | 102 | 105 | 102 | 109 | 102 |
| 9 |  |  |  |  |  | 101 | 99 | 105 | 95 | 103 | 93 | 101 |
| 12 |  |  |  |  |  |  |  |  | 97 | 105 |  |  |

D) Use of the Tissue Glues of the Invention in the Reduction or Prevention of Tissue Adhesions To investigate the effects of these improved tissue glues on the prevention or reduction of postoperative tissue adhesions, an improved tissue glue of the following composition was produced as an example:

Fibrinogen component containing:
  90 mg/ml fibrinogen concentrate,
  100 mmol/l NaCl,
  20 mmol/l Na$_3$ citrate×2H$_2$O,
  237 mmol/l-arginine×HCl and
  80 mmol/l ε:-aminocaproic acid or 1 000 KIU/ml aprotinin Factor XIII component containing:
  120 U/ml Factor XIII concentrate,
  10 mmol/l Na$_3$ citrate×2H$_2$O,
  50 m/mol/l L-histidine Thrombin component containing:
  1500 lU/ml thrombin concentrate,
  150 mmol/l NaCl,
  40 mmol/l CaCl2,
  110 mmol/l mannitol,
  5 mmol/l L-histidine.

The pH after mixing the components to give the tissue glue was about 7.4.

The use of this tissue glue in operations is described by way of example below.

Example 7

Prevention of Adhesions on the Horn of the Uterus

After opening the abdominal cavity of 12 female rabbits under anesthesia, longitudinal incisions were made in the horns of the uteri. The incisions were closed again with surgical suture material. Six rabbits were assigned to each of the two treatment groups as follows: 1—No treatment, and 2—Treatment with improved tissue glue. The wounds in the second group were each completely covered with tissue glue. After closure of the abdominal cavity, the animals were allowed to return to consciousness. After euthanasia of the rabbits after 7 days, the adhesions of the uteri with the surrounding tissue were assessed. Adhesions of the two incisions together were excluded from the evaluation. The results of the investigation are shown in Table 4.

The untreated animals showed adhesions in 63.6% of the cases. A distinct reduction in adhesions were observed in the group treated with improved tissue glue. The frequency of adhesions in this group was only 11.1%.

TABLE 4

Uterine adhesions with the surrounding tissue after treatment with tissue glues

| | 1. No treatment | 2. Improved tissue glue |
|---|---|---|
| Frequency of adhesions | 63.6% | 11.1% |

Example 8

Prevention of Adhesions an the Horn of the Uterus

In this experiment, the improved tissue glue was compared with a commercial glue (Beriplast® P) and no treatment on a total of 36 rabbits. Three groups each of 12 animals were formed in accordance with the method described in Example 7, and one horn of the uterus of each animal was treated as follows: 1—No treatment, 2.—Beriplast® P, 3—Improved tissue glue. The frequency and extent of the adhesions were assessed on day 7. The results are summarized in Table 5.

All the animals in the group which received no treatment with a tissue glue showed adhesions (100%). The rabbits treated with Beriplast® P had a distinctly lower frequency of adhesions (75%). The lowest frequency of adhesions was observed in the group of animals treated with improved tissue glue. The extent of the adhesions (length in cm) revealed similar findings.

TABLE 5

Adhesion of uterus with the surrounding tissue after treatment with fibrin glues

| | 1. No treatment | 2. Beriplast ® P | 3. Improved tissue glue |
|---|---|---|---|
| Adhesion frequency (%) | 100% | 75% | 50% |
| Length of the adhesions (cm) | 1.52 | 1.03 | 0.67 |

Example 9

Prevention of Adhesions on the Horn of the Uterus

In another experiment, improved tissue glues are compared with a commercial glue (Beriplast® P) and an untreated control. Several groups each of 12 animals were formed in accordance with the method described in Example 8, using only one horn of the uterus of each animal. The animals were treated as follows:

1. No treatment
2. Beriplast® P
3. Improved tissue glue
4. Improved tissue glue (aprotinin in place of EACA)
5. Improved tissue glue with reduced plasminogen content The frequency and the extent of the adhesions were assessed on day 7. Table 6 shows the results of the study.

About two-thirds of the animals which received no treatment with a tissue glue showed adhesions (66.7%). A distinctly lower frequency of adhesions or the lowest adhesion frequency was observed in the group of animals treated with improved tissue glues. The extent of the adhesions (length in cm) revealed similar findings.

TABLE 6

Adhesions of the uterus with the surrounding tissue after treatment with various fibrin glues (mean for n = 12 animals)

| | 1. Untreated control | 2. Beriplast® P | 3. Improved tissue glue | 4. Improved tisuse glue (aprotinin in place of EACA) | 5. Improved tissue glue with reduced plasminogen content |
|---|---|---|---|---|---|
| Adhesion frequency (%) | 66.7% | 41.7% | 33.3% | 16.7% | 0% |

TABLE 6-continued

Adhesions of the uterus with the surrounding tissue
after treatment with various fibrin glues
(mean for n = 12 animals)

|  | 1. Untreated control | 2. Beriplast ® P | 3. Improved tissue glue | 4. Improved tisuse glue (aprotinin in place of EACA) | 5. Improved tissue glue with reduced plasminogen content |
|---|---|---|---|---|---|
| Length of the adhesions (cm) | 0.59 | 0.19 | 0.26 | 0.13 | 0 |

Example 10

Prevention of Adhesions on the Horn of the Uterus

In this experiment, several groups of 8 animals were formed in accordance with the method described in example 1 and underwent operation of both horns of the uteri. Improved tissue glues were compared with a control group without treatment on 16 horns of the uteri in each group. The following treatment groups were compared:
1. No treatment
2. Improved tissue glue with reduced plasminogen content
3. Improved tissue glue with a plasminogen content which was initially reduced and was made up gain before use Only horns of the uterus which did not adhere to the incision in the other horn of the uterus were evaluated. The results of this series of tests (see Table 7 show that the reduction in the plasminogen concentration can further improve the antiadhesive properties of a fibrin glue.

TABLE 7

Prevention of adhesions on the horn of the uterus by
treatment with fibrin glues (means)

|  | 1. No treatment | 2. Improved tissue glue with reduced plasminogen content | 3. Improved tissue glue after reducing plasminogen content and making up again with plasminogen |
|---|---|---|---|
| Adhesion frequency (%) | 68.6% | 15.4% | 46.2% |
| Length of the adhesions (cm) | 0.53 | 0.07 | 0.32 |

Example 11

Prevention of Adhesions After Liver Resection 14 rabbits were anesthetized and, after opening of the abdominal cavity, the liver was exposed. A piece of about 3.5 g was resected from a lobe of the liver, resulting in a wound of about 4 cm². The wound was completely covered with a tissue glue to stop the bleeding, with 7 rabbits in each case receiving Beriplast® P or improved tissue glue. The number of animals in which the bleeding was completely stopped was recorded over 5 minutes. The abdominal cavity was then closed again and the anesthesia was terminated. After euthanasia of the animals after 7 days, the adhesions of the liver with the adjoining tissue were assessed.

Table 8 shows that the number of adhesions in the group treated with improved tissue glue was distinctly less than in the group treated with Beriplast® P. All the animals showed complete stoppage of the bleeding.

TABLE 8

Hemostasis and adhesion of the liver with the surrounding
tissue after treatment with tissue glues

|  | 1. Beriplast ® P | 2. Improved tisuse glue |
|---|---|---|
| Number of animals with adhesions | 5/7 (71.4%) | 2/7 (28.6%) |
| Number of animals with complete stoppage of bleeding | 7/7 (100%) | 7/7 (100%) |

We claim:

1. A method for reducing or preventing tissue adhesions comprising the application to a tissue of a tissue glue, wherein the tissue glue comprises:

a fibrinogen preparation, and a thrombin preparation, wherein the fibrinogen preparation can be stored in the liquid or frozen state, wherein the fibrinogen preparation further comprises a chaotropic substance in the range of more than about 0.04 M to less than about 0.28 M, wherein the total concentration of water-soluble inorganic salts in the fibrinogen preparation is equal to or less than about 100 mmol/liter; and wherein the tissue glue reduces or prevents tissue adhesions.

2. The method according to claim 1, wherein the tissue glue further comprises coagulation Factor XIII.

3. The method according to one of claims 1 or 2, wherein the tissue glue further comprises an antifibrinolytic agent.

4. The method according to claim 3, wherein the antifibrinolytic agent is ε-aminocaproic acid.

5. The method according to claim 3, wherein the antifibrinolytic agent is p-aminomethylbenzoic acid.

6. The method according to claim 3, wherein the antifibrinolytic agent is aprotinin.

7. The method according to one of claims 1 or 2, wherein the preparation of the fibrinogen preparation comprises, purification steps.

8. The method according to claim 7, wherein the fibrinogen preparation has a reduced plasminogen content.

9. The method according to claim 8, wherein the ratio of plasminogen to fibrinogen is less than $1.8 \times 10^{-4}$ (w/w).

10. The method according to claim 2, wherein the Factor XIII preparation further comprises one or more substances selected from stabilizers or buffer substances.

11. The method according to claim 10, wherein the one or more stabilizers are selected from physiologically tolerated salts of an organic di-, tri- and tetracarboxylic acid.

12. The method according to claim 11, wherein the carboxylic acid is citric acid.

13. The method according to claim 10, wherein the Factor XIII preparation further comprises one or more stabilizers selected from:
- a mono- or disaccharide or a sugar alcohol,
- at least one amino acid selected from glycine, glycylglycine, alanine, cysteine, histidine, glutamine or a physiologically tolerated salt of glutamic or aspartic acid,
- a reducing or oxidation-preventing agent, and
- a surface-active substance.

14. The method according to one of claims 1 or 2, wherein the one or more chaotropic substances is selected from arginine, guanidine, citrulline, urea, nicotine amide, and their derivatives.

15. The method according to one of claims 1 or 2, wherein the fibrinogen preparation further comprises one or more stabilizers selected from:
- an inorganic salt,
- one or more physiologically tolerated salts of organic carboxylic acids,
- one or more amino acids,
- a mono- or disaccharide, and
- a sugar alcohol.

16. The method according to claim 15, wherein the carboxylic acid is selected from citric acid and lactic acid.

17. The method according to one of claims 1 or 2, wherein the thrombin preparation further comprises one or more stabilizers.

18. The method according to claim 17, wherein the one or more stabilizers are selected from: a soluble calcium salt,
- sodium chloride,
- a buffer substance,
- a sugar,
- a sugar alcohol,
- an amino acid,
- a salt of a mono- or polycarboxylic acid, and
- a salt of a mono- or polyhydroxy carboxylic acid.

19. The method according to claim 17, wherein the stabilizer is a non-covalently binding inhibitor.

20. The method according to one of claims 1 or 2, wherein the preparation of the thrombin preparation comprises purification by hydrophobic interaction chromatography.

21. The method according to claim 20, wherein the purification of the thrombin preparation further comprises purification by cation exchange chromatography.

22. The method according to one of claims 1 or 2, wherein the tissue glue or the constituents of the tissue glue have been subjected to one or more methods for inactivating or removing viruses.

23. The method according to claim 3, wherein the tissue glue or the constituents of the tissue glue have been subjected to one or more methods for inactivating or removing viruses.

24. A method for reducing or preventing tissue adhesions comprising the application to a tissue of a tissue glue, wherein the tissue glue comprises:
- a fibrinogen preparation,
- a thrombin preparation, wherein the fibrinogen preparation can be stored in liquid or frozen state, wherein the fibrinogen preparation has a reduced plasminogen content, wherein the total concentration of water-soluble inorganic salts in the fibrinogen preparation is egual to or less than about 100 mmol/liter; and wherein the tissue glue reduces or prevents tissue adhesions.

25. The method according to claim 1, wherein the tissue has optionally been treated with a conventional tissue glue prior to the application of the tissue glue of claim 1.

26. The method according to claim 24, wherein the tissue has optionally been treated with a conventional tissue glue prior to the application of the tissue glue of claim 24.

27. The method according to claim 2, wherein the total concentration of water-soluble inorganic salts in the fibrinogen preparation is equal to or less than about 50 mmol/liter.

28. The method according to claim 27, wherein the total concentration of water-soluble inorganic salts in the fibrinogen preparation is equal to or less than about 20 mmol/liter.

29. The method according to claim 28, wherein no water-soluble inorganic salts are added to the fibrinogen preparation.

30. The method according to claim 2, wherein the fibrinogen preparation remains stable after 2 weeks of storage in the liquid state.

* * * * *